United States Patent [19]

Comben

[11] 4,310,001
[45] Jan. 12, 1982

[54] CONNECTOR ASSEMBLY FOR BODY IMPLANTABLE MEDICAL SYSTEMS

[75] Inventor: Richard H. Comben, Minneapolis, Minn.

[73] Assignee: Medtronic, Inc., Minneapolis, Minn.

[21] Appl. No.: 142,402

[22] Filed: Apr. 21, 1980

[51] Int. Cl.³ ............................................. A61N 1/00
[52] U.S. Cl. ............................ 128/419 P; 128/202.27; 128/260
[58] Field of Search .................... 128/202.27, 213, 260, 128/419 P

[56] References Cited

U.S. PATENT DOCUMENTS

| | | | |
|---|---|---|---|
| 3,533,403 | 10/1970 | Woodson | 128/419 P |
| 3,757,789 | 9/1973 | Shanker | 128/419 P |
| 4,105,037 | 8/1978 | Richter et al. | 128/419 P |

*Primary Examiner*—William E. Kamm
*Attorney, Agent, or Firm*—Schroeder, Siegfried, Vidas, Steffey & Arrett

[57] ABSTRACT

A connector assembly for a body implantable medical system which interconnects a medical agent providing subsystem with a medical agent delivering subsystem. The connector assembly establishes an interconnected contact force between the medical agent providing and delivering subassemblies that is operator independent. In a preferred embodiment, the connector assembly is formed as an over-center toggle carried by the delivering subassembly. The toggle may be formed of first and second legs, the first leg being a beam spring pivotally secured adjacent one end of the second leg. The other end of the beam spring may be anchored to the medical providing subassembly while that subassembly and the second leg other end are provided with cooperating arcuate bearing surfaces. Relative motion of the bearing surfaces, as by a force applied to the second leg, will cause the toggle to approach and pass through an over-center position to provide a secure mechanical connection between the medical agent providing subsystem and a delivery subsystem which carries the connector assembly.

15 Claims, 9 Drawing Figures

CONNECTOR ASSEMBLY FOR BODY IMPLANTABLE MEDICAL SYSTEMS

DESCRIPTION

BACKGROUND OF PRIOR ART

Body implantable medical systems are known to the prior art. Such systems have taken the form of electrical stimulators having a first subsystem (a signal generator) which provides a medical agent (electrical energy) and a second subsystem (an electrode carrying lead) which delivers the medical agent to the desired body site. In other systems, the medical agent may be a medicinal fluid or infusate which is provided by a pump or reservoir and delivered to the desired body site by a catheter.

One requirement of systems of the type described above is that the providing and delivering subsystems be reliably interconnected. In the context of a body implantable electrical stimulator, the generator and lead must not only be mechanically secured to each other but must be secured in a manner which allows a reliable electrical contact between those subsystems. When fluids are to be dispensed, the subsystem interconnection must allow a fluid flow from the providing to the delivering subsystem.

Typical prior art interconnection techniques have imposed severe design constraints on techniques of body implantable medical systems. For example, and again in the context of a body implantable electrical stimulator, the increasing miniaturization of the electronics necessary to provide the desired stimulation energy has allowed the design of increasingly sophisticated signal generators of smaller size. However, the size requirements of prior art connector assemblies has limited the ability to maximize the size reduction of the overall unit. Also, the connector assemblies known to the prior art are commonly formed of polymeric materials which are far more difficult to sterilize than the hermetically sealed metal canisters which typically house the stimulator electronics. Further, typical prior art electrical stimulation connector assemblies are operator sensitive in that the contact force is established in accordance with the degree of manipulation by an operator.

BRIEF SUMMARY OF THE INVENTION

The present invention provides a connector assembly for a body implantable medical system which establishes a reliable mechanical interconnection between the medical agent providing subsystem and the delivery subsystem. The connector assembly may be carried by the delivery subsystem to facilitate reworking of the medical agent providing subsystem while being of sufficiently small size as to allow placement of the delivery subsystem in accordance with known techniques. The connector assembly establishes an interconnected contact force between the medical agent providing and delivery subsystems that is independent of the degree of operator manipulation. In a preferred embodiment, the connector assembly is an over-center toggle formed of a beam spring and clip pivotally secured to each other. One end of the beam spring may be anchored to the housing of the medical agent providing subsystem with that subsystem having an arcuate surface to provide a bearing surface in which the clip may be pivoted. With the spring anchored, the clip is pivoted to and through a line generally through the spring anchor location and the pivot axis of the clip to interconnect the medical agent providing and delivering subsystems. Electrical and/or fluid interconnections may be provided for, as required.

DETAILED DESCRIPTION OF THE INVENTION

Figure 1:
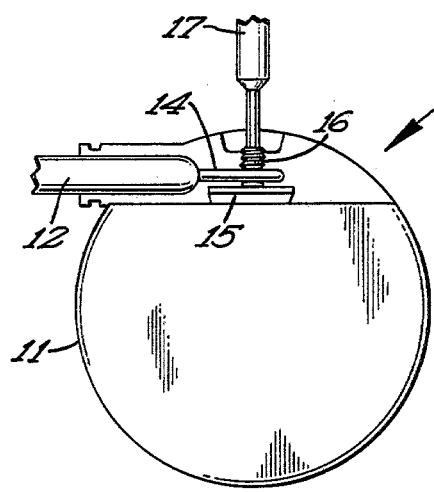
FIG. 1 illustrates a typical prior art electrical stimulator connector assembly.

Referring now to FIG. 1, there is illustrated a typical prior art connector assembly for a body implantable electrical stimulator, the stimulator being indicated generally at 10. The stimulator is formed of a signal generator 11 and electrode carrying lead 12, in known manner. A connector assembly 13 is carried by the signal generator 11 and is typically formed as a molded part—either molded in place or formed as a preformed part secured to the signal generator 11. The connector assembly 13 accepts one end of the lead 12, the lead 12 terminating at a pin 14. Within the connector assembly 13, the pin 14 engages an electrical contact 15 against which it may be urged by a set screw 16. A tool 17 is insertable within a recess in the connector assembly 13 to engage the set screw and, upon manipulation of the tool 17, the set screw is driven into mechanical and electrical contact with the pin 14. However, the degree and reliability of that contact is dependent upon the force applied via the tool 17. In some instances, the force may be insufficient to provide a reliable mechanical securement. In other instances, the force may be excessive resulting in a stripping of the threads with which the set screw 16 cooperates. In all cases, the use of a polymer to form the connector assembly 13 hampers a reworking of a once-implanted unit in that polymeric materials are much more difficult to sterilize than are the exposed surfaces of the metallic canister in which the signal generator 11 is typically housed.

Figure 2:
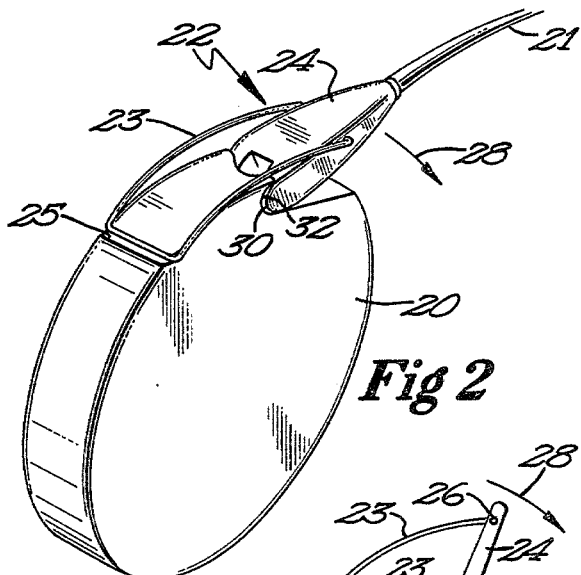
FIG. 2 illustrates a preferred embodiment of the present invention.

FIG. 2 illustrates a preferred embodiment of the present invention which provides a secure mechanical interconnection between a medical agent providing subsystem and a medical agent delivering subsystem such as the signal generator and lead discussed with reference to FIG. 1. In FIG. 2, reference numeral 20 designates a medical agent providing subsystem which may take the form of a signal generator. Alternatively, the subsystem 20 may be a reservoir or pump for a medicinal fluid. In some contexts, it may be desirable for the medical agent providing subsystem 20 to function as both an electrical signal and medicinal fluid providing subsystem.

A delivery subsystem 21 which may be either an electrical lead or catheter, or both, is illustrated in FIG. 2 carrying at its proximal end a connector assembly indicated generally at 22. The connector assembly is an over-toggle device formed of a beam spring 23 and clip member 24, the spring and clip being pivotally secured to each other. The beam spring 23 is a curved U-shaped member, the non-pivoted end of which is anchored in a groove 25 in the outer surface of the medical agent providing subsystem 20.

Figure 3:
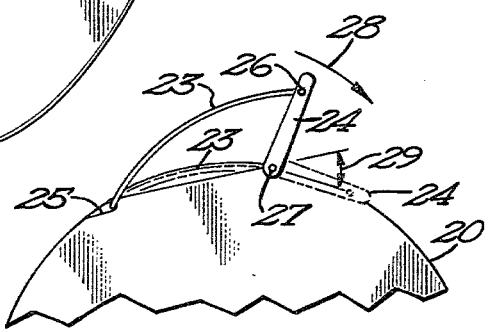
FIG. 3 illustrates the interaction of the components of the preferred embodiment of FIG. 2.

FIG. 3 diagrammatically illustrates the cooperation between the elements forming the present invention. The groove 25 engages the U-shaped end of the spring 23 to pin or anchor that end. The other end of the spring 23 is pivotally connected to the clip 24 at 26. The clip 24 is pivotable about a pivot axis 27, in a manner to be described more fully below, and pivots between the position illustrated in solid lines in FIG. 3 and the position illustrated in phantom in that figure. A force on the clip 24 acting in the direction of the arrow 28 will pivot the clip 24 and cause it to approach a line drawn generally through the pinned or anchored end of spring 23 and the pivot axis 27 of the clip 24. The line 29 indicates the center position of the toggle mechanism. As the force continues to move the clip 24, the clip 24 will pass the line 29 at which time the force of the spring 23 will act to maintain the clip 24 against the surface of subsystem 20 in the over-center position illustrated in phantom in FIG. 3. In this position, the clip 24 is reliably secured to the outer surface of subsystem 20.

Figure 4:
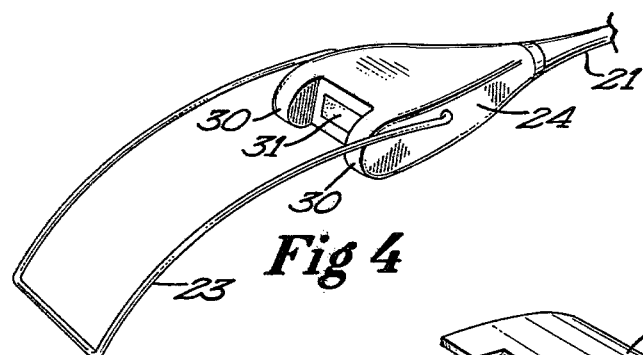
FIG. 4 illustrates a portion of the preferred embodiment illustrated in FIG. 2.

FIG. 4 illustrates a preferred embodiment of the clip/spring forming a portion of the present invention. Specifically, a clip 24 is carried at one end of a medical agent delivering subsystem 21, the subsystem 21 being an electrode carrying lead or catheter, or both. A curved beam spring 23 is pivotally secured to the clip 24. Arcuate bearing surfaces 30 are provided on the clip 24, the bearing surfaces 30 allowing a pivotal movement of the clip 24 as about a pivot axis (see axis 27 in FIG. 3) in a manner to be described more fully below. Intermediate the bearing surfaces 30 is a contact region 31, the contact region 31 being in electrical and/or fluid conducting communication with the subsystem 21 in a manner to be described more fully below.

Figure 5:
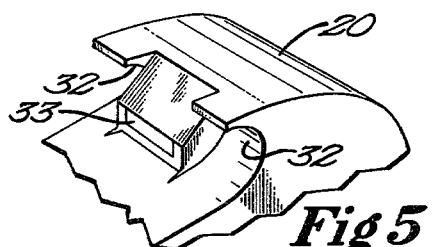
FIG. 5 illustrates another portion of the preferred embodiment illustrated in FIG. 2.

Referring now to FIG. 5, there is illustrated a portion of the subsystem 20 that is intended for cooperation with the clip/spring combination illustrated in FIG. 4. Arcuate bearing surfaces 32 are provided in the surface of subsystem 20 and are adapted for cooperation with the bearing surfaces 30 of the clip 24 such that with the bearing surfaces 30 of clip 24 in engagement with the bearing surfaces 32 of subsystem 20, the clip 24 may be pivoted relative to the subsystem 20 about a pivot axis (see axis 27 in FIG. 3). Intermediate the bearing surfaces 32 there is provided a contact region 33 by which communication with the components contained within the subassembly may be established, in a manner to be described more fully below. However, with the bearing surfaces 30 of clip 24 in engagement with the bearing surfaces 32 of subsystem 20 and with the clip 24 in the over-center position illustrated in phantom in FIG. 3, the contact regions 31 and 33 are in cooperating relation with each other to establish a communication between the subsystem 20 medical agent providing elements and the delivering subsystem 21.

Figure 6:
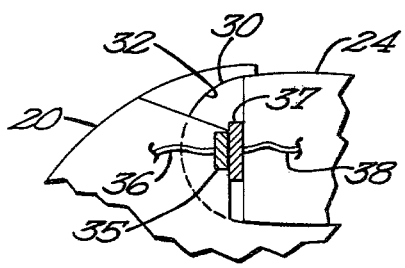

FIGS. 6–9 illustrate alternative forms of cooperation between the contact regions 31 and 33. In FIG. 6, an electrical contact 35 is carried at the contact region 33 and is in electrical communication with the subsystem 20 components via a lead 36. Similarly, a contact 37 is carried at the contact region 31 and is in electrical communication with an electrode carried by the delivery subsystem 21 via a lead 38. On positioning of the clip bearing surfaces 30 against the bearing surfaces 32 of subsystem 20 and rotation of the clip to the over-center position illustrated in phantom in FIG. 3, the contacts 35 and 37 will engage each other and establish an electrical communication between the leads 36 and 38.

Figure 7:
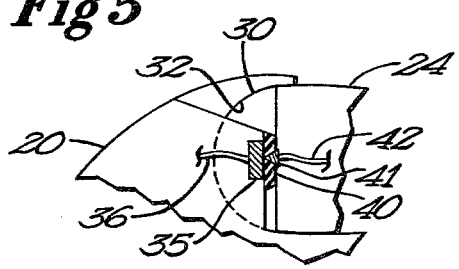

A slightly different electrical communication system is illustrated in FIG. 7 in which a contact 35 is carried in the contact region 33 having a cooperating lead 36, as in FIG. 6. However, the contact 35 is covered by an insulating material 40. The material 40 may be any known material suitable for the body environment. A pointed contact 41 projects from the contact region 31 of clip 24 and, on pivoting of the clip 24 to the over-center position, the contact 41 will pierce the insulating material 40 to establish an electrical communication with the contact 35. The contact 41 has a cooperating lead 42 similar to lead 38 of FIG. 6. With the configuration illustrated in FIG. 7, two or more independent electrical contacts may be established and their integrity assured.

Figure 8:
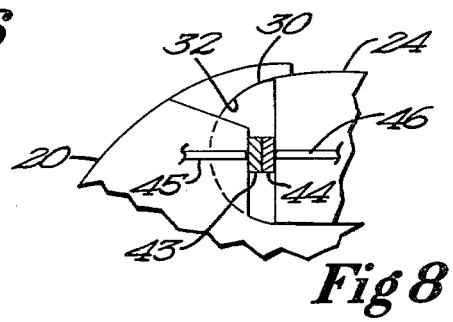

FIG. 8 illustrates hydraulic couplings 43 and 44 carried at the contact areas 33 and 31, respectively. Each of the couplings 43 and 44 have a cooperating conduit 45 and 46, respectively, the conduits establishing a fluid passage, with the couplings 43 and 44, between the subassemblies 20 and 21.

Figure 9:
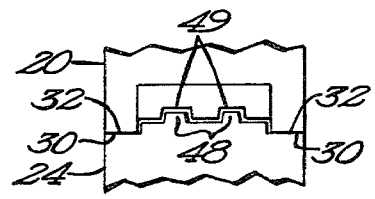
FIGS. 6-9 illustrate alternative cooperation modes between those portions of the preferred embodiment that are illustrated in FIGS. 4 and 5.

FIG. 9 is a top view of the cooperation of the contact areas 31 and 33 with the contact area 31 being provided with projections 48 while contact area 33 is provided with cooperating recesses 49 such that a labyrinth-type structure results. Communication between the subsystems 20 and 21 may be established between the projections 48 and recesses 49 with those projections and recesses facilitating an isolation of the elements establishing those communications.

Obviously, many modifications and variations of the present invention are possible in light of the above teachings. For example, it is presently contemplated that a hold-down device will be employed to maintain the clip 24 in the over-center position to combat the well-known twiddler's syndrome. This device may take the form of a band which holds the clip in the over-center position. Additionally, various design parameters such as clip length and spring strength and curvature may be varied to establish the optimum contact force between the contact regions 31 and 33, dependent on the type of contact it is desired to establish and maintain. In any event, that contact force will be established by the physical parameters of the system components as opposed to operator manipulation. It is therefore to be understood that, within the scope of the appended claims, the invention may be practice otherwise than as specifically described.

I claim:

1. In a body implantable medical system of the type having means for providing a medical agent, means for delivering said medical agent to a desired body site and means interconnecting said medical agent providing and delivering means, the improvement wherein said interconnecting means comprises over-center toggle means.

2. The body implantable medical system of claim 1 wherein said medical agent comprises electrical energy.

3. The body implantable medical system of claim 1 wherein said medical agent comprises medicinal fluid means.

4. The body implantable medical system of claim 3 wherein said medical agent further comprises electrical energy.

5. The body implantable medical system of claim 1 wherein said toggle means is carried by said delivering means.

6. The body implantable medical system of claim 1 wherein said toggle means comprises spring means and clip means.

7. The body implantable medical system of claim 6 wherein said spring means comprises beam spring means pivotally secured to said clip means.

8. The body implantable medical system of claim 7 wherein said toggle means is carried by said delivering means.

9. The body implantable medical system of claim 7 wherein said beam spring means comprises curved beam spring means.

10. The body implantable medical system of claim 9 wherein said toggle means is carried by said delivering means.

11. The body implantable medical system of claim 1 wherein said toggle means comprises beam spring means and clip means, one end of said beam spring means being pivotally secured adjacent one end of said clip means, the other end of said clip means comprising arcuate bearing surface means.

12. The body implantable medical system of claim 11 wherein said medical agent providing means comprises: means for engaging the other end of said beam spring means; and arcuate bearing surface means for cooperation with said clip means bearing surface means to allow pivotal motion of said clip means relative to said medical agent providing means.

13. The body implantable medical system of claim 12 wherein said beam spring means comprises curved beam spring means.

14. The body implantable medical system of claim 13 wherein said toggle means is carried by said delivering means.

15. The body implantable medical system of claim 12 wherein said clip means is pivotable, relative to said medical agent providing means, to move said one end of said clip through a line extending generally through the beam spring means engaging means and said clip means arcuate bearing surface means pivot axis.

* * * * *